(12) United States Patent
Cheng et al.

(10) Patent No.: US 11,555,027 B1
(45) Date of Patent: Jan. 17, 2023

(54) METHOD FOR PREPARING 6-AMINO-4-[[3-CHLORO-4-(PYRIDIN-2-YLMETHOXY)PHENYL]AMINO]-7-ETHOXYLQUINOLINE 3-CARBONITRILE

(71) Applicant: JIANGSU OCEAN UNIVERSITY, Jiangsu (CN)

(72) Inventors: Qingfang Cheng, Jiangsu (CN); Chenlin Hua, Jiangsu (CN); Jinlu Zhong, Jiangsu (CN); Qifa Wang, Jiangsu (CN); Shoushuai Qiu, Jiangsu (CN); Luyao Qi, Jiangsu (CN); Wanqing Song, Jiangsu (CN); Yesong Zhang, Jiangsu (CN)

(73) Assignee: JIANGSU OCEAN UNIVERSITY, Jiangsu (CN)

( * ) Notice: Subject to any disclaimer, the term of this patent is extended or adjusted under 35 U.S.C. 154(b) by 0 days.

(21) Appl. No.: 17/558,501

(22) Filed: Dec. 21, 2021

(30) Foreign Application Priority Data

Jun. 29, 2021 (CN) .......................... 202110730320.2

(51) Int. Cl.
*C07D 401/12* (2006.01)
(52) U.S. Cl.
CPC ................................. *C07D 401/12* (2013.01)

(58) Field of Classification Search
CPC ..................................................... C07D 401/12
USPC ........................................................... 546/171
See application file for complete search history.

(56) References Cited

FOREIGN PATENT DOCUMENTS

WO         9633980        10/1996
WO        2005028443        3/2005

*Primary Examiner* — Kahsay Habte
(74) *Attorney, Agent, or Firm* — JCIP Global Inc.

(57) ABSTRACT

The present invention relates to the technical field of pharmaceutical synthesis, and in particular, to a method for preparing 6-amino-4-[[3-chloro-4-(pyridin-2-ylmethoxy)phenyl]amino]-7-ethoxylquinoline 3-carbonitrile. In the present invention, Compound 3 and Compound 2 react in the presence of a sulfonic compound to give Compound 4; Compound 4, 4-nitro-3-ethoxylphenylamine and triethyl orthoformate react by heating at reflux to give a solid intermediate; the solid intermediate and a Lewis acid are heated for a ring-closing reaction to give Compound 5; Compound 5, hydrazine hydrate and activated carbon react in the presence of a catalyst to give Compound 1, which is (6-amino-4-[[3-chloro-4-(pyridin-2-ylmethoxy) phenyl]amino]-7-ethoxylquinoline 3-carbonitrile). The present invention has advantages of a short reaction route, a high yield and simple procedures, requires no extreme reaction condition, and features higher cost-efficiency and suitability for industrial manufacture.

11 Claims, No Drawings

METHOD FOR PREPARING 6-AMINO-4-[[3-CHLORO-4-(PYRIDIN-2-YLMETHOXY)PHENYL]AMINO]-7-ETHOXYLQUINOLINE 3-CARBONITRILE

CROSS-REFERENCE TO RELATED APPLICATION

The present application is based on and claims the priority benefits of China application No. 202110730320.2, filed on Jun. 29, 2021. The entirety of the above-mentioned patent application is hereby incorporated by reference herein and made a part of this specification.

Technical Field

The present invention relates to the technical field of pharmaceutical synthesis, and in particular, to a method for preparing 6-amino-4-[[3-chloro-4-(pyridin-2-ylmethoxy) phenyl]amino]-7-ethoxylquinoline 3-carbonitrile.

Description of Related Art

4-Amino-quinoline-3-carbonitrile derivatives are important intermediates for preparing tyrosine kinase inhibitors of a 3-cyanoquinoline parent structure, including bosutinib, neratinib, pelitinib and pyrotinib. The chemical name of pyrotinib is (R,E)-N-(4-(3-chloro-4-(pyridin-2-ylmethoxy) phenylamino)-3-cyano-7-ethoxyquinolin-6-yl)-3-(1-methylpyrrolidin-2-yl) acrylamide, which is clinically used in the form of a maleate salt (1:2). Pyrotinib maleate, sold in the trade name of Airuini, is an oral irreversible tyrosine kinase inhibitor developed by Jiangsu Hengrui Pharmaceuticals Co., Ltd. In August, 2018, pyrotinib was approved by China Food and Drug Administration (CFDA, now known as National Medical Products Administration, or NMPA) for the treatment of HER2-positive, previously untreated or trastuzumab-treated relapsed or metastatic breast cancer in combination with capecitabine. Pyrotinib also has activity against EGFR, HER1, HER2 and HER4 and is thus known as oral Herceptin.

6-Amino-4-[[3-chloro-4-(pyridin-2-ylmethoxy)phenyl] amino]-7-ethoxylquinoline 3-carbonitrile is an important intermediate for preparing pyrotinib. By the acylation reaction between 6-amino-4-[[3-chloro-4-(pyridin-2-ylmethoxy) phenyl]amino]-7-ethoxylquinoline 3-carbonitrile and 2-(diethoxyphosphoryl)acetic acid and the Witting reaction between the resulting N-[4-[[3-chloro-4-(pyridin-2-ylmethoxy)phenyl]amino]-3-cyano-7-ethoxyquinolin-6-yl]-2-(diethoxyphosphoryl) acetic acid and (2R)-1-methylpyrrolidine-2-formaldehyde, pyrotinib can be prepared. The structural formula of 6-amino-4-[[3-chloro-4-(pyridin-2-ylmethoxy) phenyl]amino]-7-ethoxylquinoline 3-carbonitrile (Compound1) is:

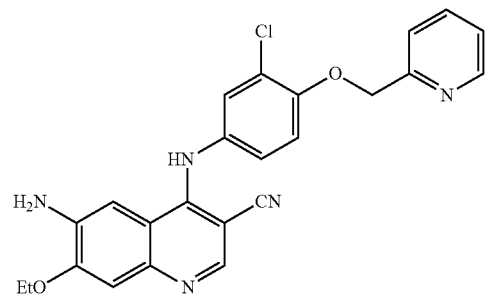

1

Patent Nos. WO2005028443A2 and WO9633980 disclosed a process for synthesizing Compound 1, which starts with 5-nitro-2-aminophenol and comprises 8 steps including amidation, alkylation, reduction, condensation, cyclization, chlorination, amination and deprotection. The synthesis is as follows:

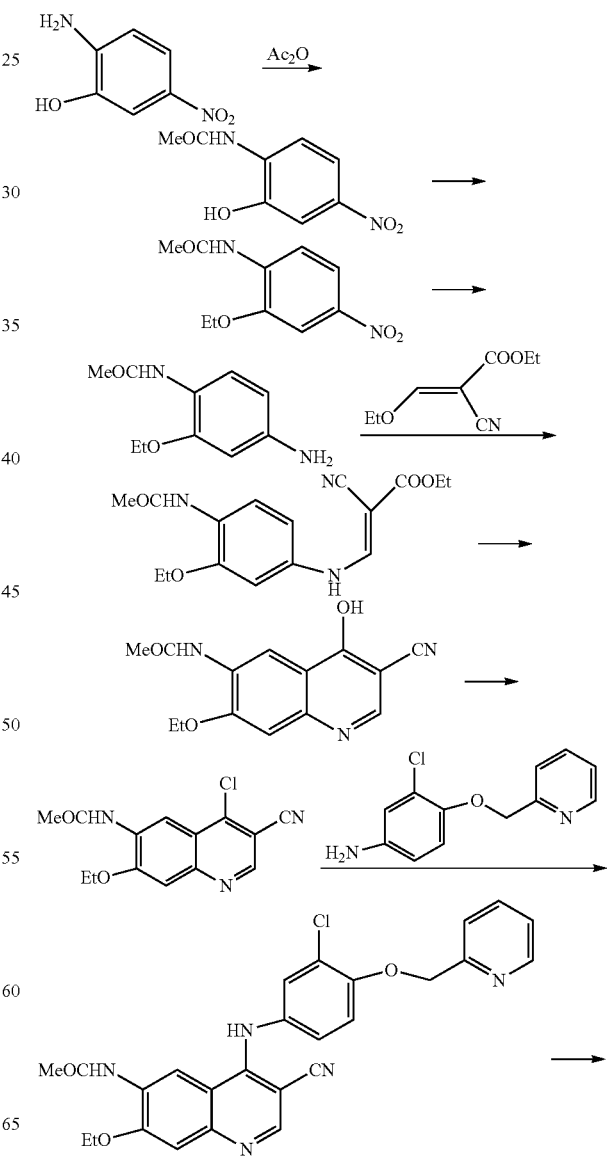

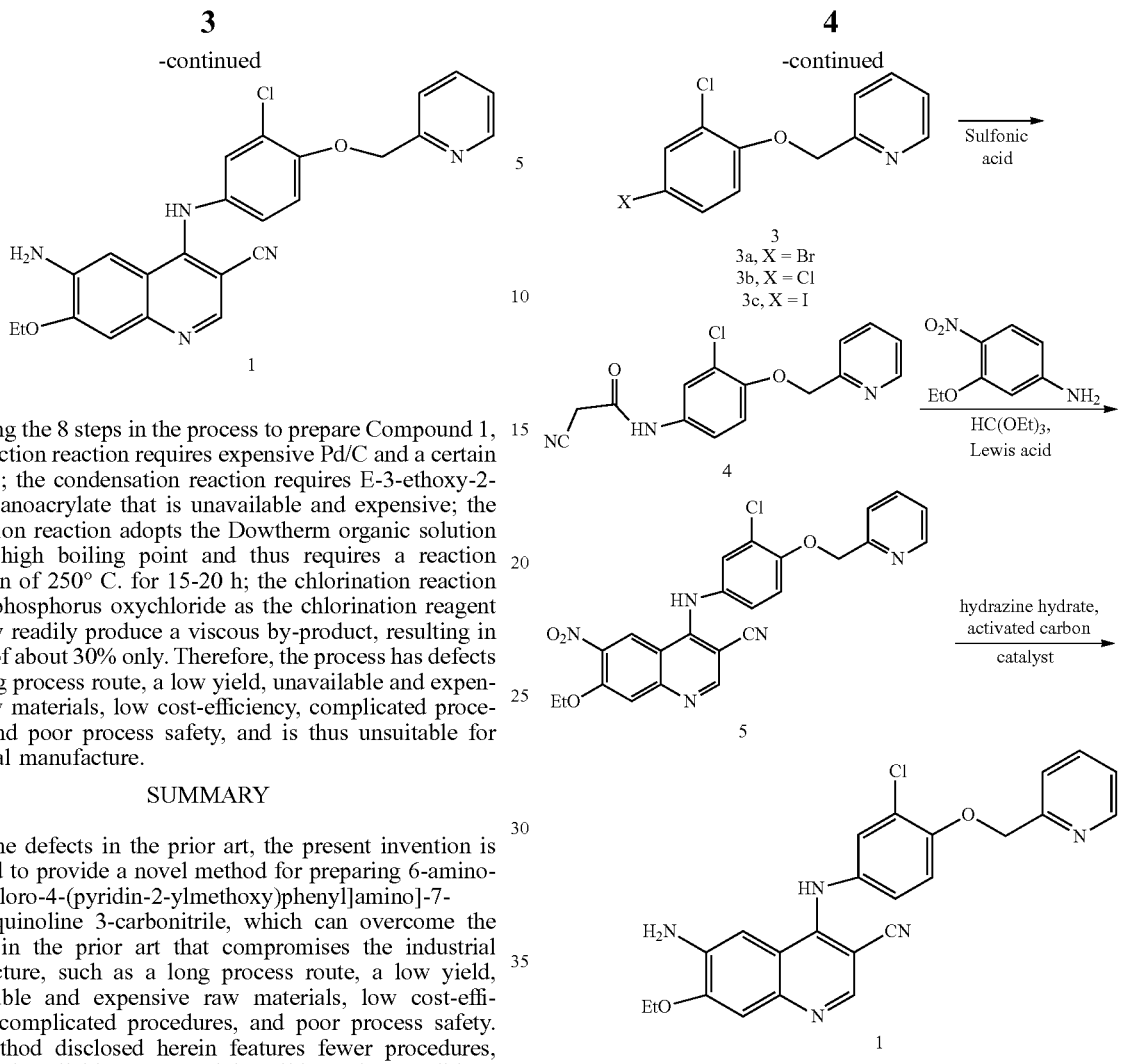

Among the 8 steps in the process to prepare Compound 1, the reduction reaction requires expensive Pd/C and a certain pressure; the condensation reaction requires E-3-ethoxy-2-ethyl cyanoacrylate that is unavailable and expensive; the cyclization reaction adopts the Dowtherm organic solution with a high boiling point and thus requires a reaction condition of 250° C. for 15-20 h; the chlorination reaction adopts phosphorus oxychloride as the chlorination reagent and may readily produce a viscous by-product, resulting in a yield of about 30% only. Therefore, the process has defects of a long process route, a low yield, unavailable and expensive raw materials, low cost-efficiency, complicated procedures and poor process safety, and is thus unsuitable for industrial manufacture.

SUMMARY

For the defects in the prior art, the present invention is intended to provide a novel method for preparing 6-amino-4-[[3-chloro-4-(pyridin-2-ylmethoxy)phenyl]amino]-7-ethoxylquinoline 3-carbonitrile, which can overcome the defects in the prior art that compromises the industrial manufacture, such as a long process route, a low yield, unavailable and expensive raw materials, low cost-efficiency, complicated procedures, and poor process safety. The method disclosed herein features fewer procedures, cheap and available raw materials, mild reaction conditions and higher cost-efficiency, and is suitable for industrial manufacture.

For the above purposes, the present invention specifically provides the following technical schemes:

step (1), subjecting Compound 2 (cyanoacetamide) and Compound 3 (2-[(4-halo-2-chlorophenoxy) methyl]pyridine) to a substitution reaction in the presence of a sulfonic compound to give Compound 4 (N-[3-chloro-4-(pyridin-2-ylmethoxy)]phenyl-2-cyanoacetamide); step (2), subjecting Compound 4, 4-nitro-3-ethoxylphenylamine and triethyl orthoformate to a condensation reaction to give a solid intermediate; heating the solid intermediate in the presence of a Lewis acid for a ring-closing reaction to give Compound 5 (6-nitro-4-[[3-chloro-4-(pyridin-2-ylmethoxy) phenyl]amino]-7-ethoxylquinoline 3-carbonitrile); and step (3), subjecting Compound 5, hydrazine hydrate and activated carbon to a reduction reaction in the presence of a catalyst to give Compound 1 (6-amino-4-[[3-chloro-4-(pyridin-2-ylmethoxy)phenyl]amino]-7-ethoxylquinoline 3-carbonitrile).

The synthesis route is as follows:

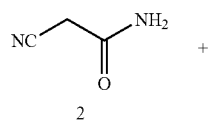

The halogen atom X in Compound 3 molecule can be chlorine (Cl), bromine (Br), iodine (I) and other halogens. For example, when X is Br, the compound is Compound 3a, when X is Cl, the compound is Compound 3b and when X is I, the compound is Compound 3c; the sulfonic acid compound in step (1) is an alkyl sulfonic acid, an aryl sulfonic acid and the like, preferably, the aryl sulfonic acid is p-toluenesulfonic acid or the alkyl sulfonic acid is methanesulfonic acid, and the molar ratio of the sulfonic acid compound to Compound 3 is (1-1.4):1.

Preferably, after the reaction in step (1) is completed, the reaction is quenched, and ammonia water is added to precipitate a solid of Compound 4 (N-[3-chloro-4-(pyridin-2-ylmethoxy)]phenyl-2-cyanoacetamide).

More preferably, the reaction temperature in step (1) is 50-80° C.

Preferably, the Lewis acid in step (2) is a halogen-containing Lewis acid, such as aluminium chloride, ferric chloride, boron trifluoride and zinc chloride, preferably aluminium chloride or boron trifluoride, and the molar ratio of the Lewis acid to Compound 4 is (2-3):1.

Preferably, the molar ratio of triethyl orthoformate to 4-nitro-3-ethoxylphenylamine to the Lewis acid to Compound 4 in step (2) is (1.05-1.3):(1.05-1.2):(2-3):1.

Preferably, the reaction of Compound 4, 4-nitro-3-ethoxylphenylamine and triethyl orthoformate in step (2) is performed in ethanol; the solid intermediate and the Lewis acid react in diethylene glycol dimethyl ether; after the reaction in step (2) is completed, the reaction mixture is mixed with ice water to precipitate a solid of Compound 5.

Preferably, the temperature of the heating ring-closing reaction of the solid intermediate and the Lewis acid in step (2) is 90-140° C.

Preferably, the catalyst in step (3) comprises ferric chloride hexahydrate and aluminium chloride hexahydrate in a molar ratio of 1:(0.1-0.4).

More preferably, the molar ratio of ferric chloride hexahydrate to Compound 5 in step (3) is 1:(6-10).

Preferably, the reaction temperature in step (3) is 50-90° C.

Preferably, the reaction in step (3) is performed in a mixed solvent of ethanol and water.

More preferably, step (3) specifically comprises:
mixing Compound 5 with a mixed solvent of ethanol and water, heating the mixture to 50-90° C., adding activated carbon and the catalyst, and raising the temperature to 50-90° C.; and
continuously adding hydrazine hydrate, and reacting the mixture at 50-90° C. to give Compound 1.

Preferably, the molar ratio of the sulfonic compound to Compound 3 in step (1) is 1.4:1, and the reaction temperature in step (1) is 80° C.;
the molar ratio of triethyl orthoformate to 4-nitro-3-ethoxylphenylamine to the Lewis acid to Compound 4 in step (2) is 1.3:1.2:3:1, and the Lewis acid is selected from aluminium chloride and boron trifluoride; the temperature of the heating ring-closing reaction of the solid intermediate and the Lewis acid is 140° C.; and
step (3) specifically comprises: mixing Compound 5 with a mixed solvent of ethanol and water, and heating the mixture to 50-60° C.; adding activated carbon and the catalyst, and raising the temperature to 75-90° C.; continuously adding hydrazine hydrate, and reacting the mixture at 75-90° C. to give Compound 1.

Beneficial effects

The present invention provides a novel method for preparing an intermediate of pyrotinib, characterized by fewer procedures, cheap and available raw materials, mild reaction conditions, higher cost-efficiency, and suitability for industrial manufacture.

The method disclosed herein also features a higher yield and simpler procedures.

DESCRIPTION OF THE EMBODIMENTS

The present invention will be further illustrated by the following specific examples below. It should be noted that the examples of the present invention are provided only for illustrating the present invention rather than limiting the scope of the present invention.

The materials or reagents used in the examples are commercially available unless otherwise specified.

Terms used herein have the following meanings.

The term "sulfonic acid compound" refers to a group of organic compounds of formula R-$SO_3$H, formed by the connection of sulfonyl and hydrocarbyl (including aryl).

The term "alkyl sulfonic acid" refers to a group of organic compounds formed by the connection of sulfonyl and alkyl, for example, methanesulfonic acid and the like.

The term "aryl sulfonic acid" refers to a group of organic compounds formed by the connection of sulfonyl and an aromatic group, for example, benzenesulfonic acid, alkyl benzenesulfonic acid and the like.

Compounds used in the examples have the following meanings.

The term "ammonia water" refers to an aqueous solution containing 25-28% of ammonia.

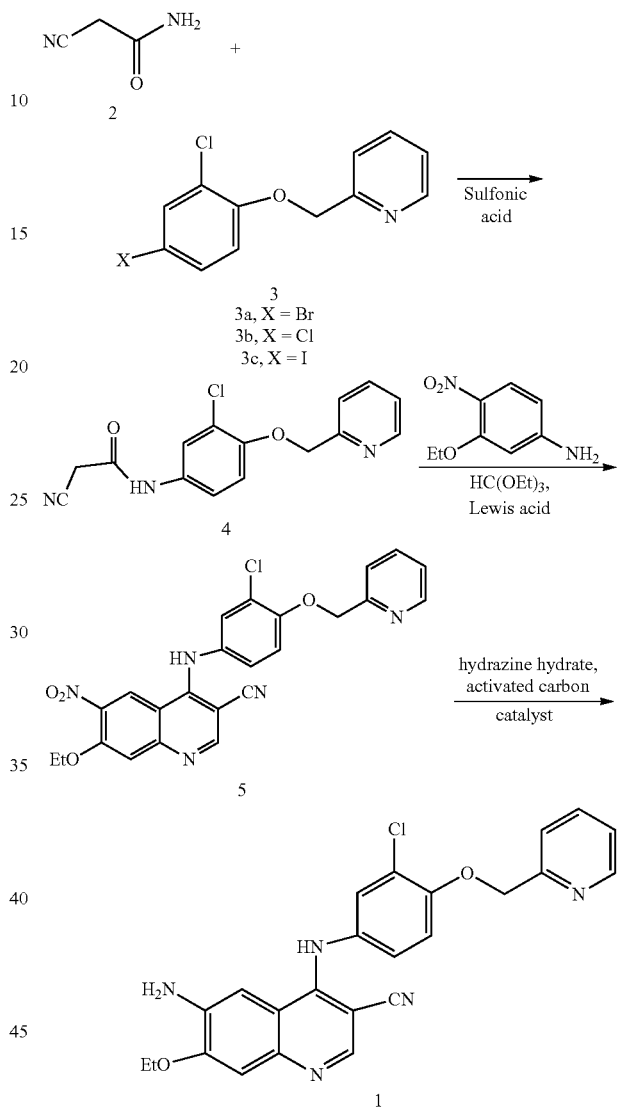

Example 1

Preparation of Compound 4 (N-[3-chloro-4-(pyridin-2-ylmethoxy)]phenyl-2-cyanoacetamide)

464 mmol of Compound 2, 400 mmol of Compound 3a, 560 mmol of p-toluenesulfonic acid and 1 L of isopropanol were added into a reaction flask. The reaction system was heated to 80° C. with stirring, and was continuously stirred at this temperature for reaction. The reaction process was monitored by TLC (thin-layer chromatography). After reaction was completed, the reaction solution was cooled to room temperature, 1.2 L of ice water was added to the reaction solution before 100 mL of ammonia water was dropwise added to the mixture with stirring. The resulting mixture was stirred for 1 hour at the room temperature and a solid was precipitated. The solid was separated by filtration and dried at reduced pressure to give Compound 4 (90% yield). The crude solid product was directly used in the next reaction without purification. A small amount of the crude solid product was purified for structure confirmation. ESI-LRMS m/z: 302.4 [M+H]$^+$, $^1$H NMR (500 MHz, DMSO-d6) δ: 3.36 (s, 2H), 5.59(s, 2H), 6.68 (d, J=2.4 Hz, 1H), 7.36-7.45(m, 2H), 7.55 (s, 1H), 7.76 (d, J=3.6 Hz, 1H), 7.94-8.11(m, 1H), 8.59 (d, J=3.6 Hz, 1H), 9.3 (s, 1H).

Example 2

Preparation of Compound 4 (N-[3-chloro-4-(pyridin-2-ylmethoxy)]phenyl-2-cyanoacetamide)

58 mmol of Compound 2, 50 mmol of Compound 3b, 70 mmol of p-toluenesulfonic acid and 120 mL of isopropanol were added into a reaction flask. The reaction system was heated to 80° C. with stirring, and was continuously stirred at this temperature for reaction. The reaction process was monitored by TLC. After reaction was completed, the reaction solution was cooled to room temperature, 120 mL of ice water was added to the reaction solution before 10 mL of ammonia water was dropwise added to the mixture with stirring. The resulting mixture was stirred for 1 hour at the room temperature and a solid was precipitated. The solid was separated by filtration and dried at reduced pressure to give Compound 4 (69% yield). The crude solid product was directly used in the next reaction without purification.

Example 3

Preparation of Compound 4 (N-[3-chloro-4-(pyridin-2-ylmethoxy)]phenyl-2-cyanoacetamide)

58 mmol of Compound 2, 50 mmol of Compound 3c, 70 mmol of p-toluenesulfonic acid and 120 mL of isopropanol were added into a reaction flask. The reaction system was heated to 80° C. with stirring, and was continuously stirred at this temperature for reaction. The reaction process was monitored by TLC. After reaction was completed, the reaction solution was cooled to room temperature, 120 mL of ice water was added to the reaction solution before 10 mL of ammonia water was dropwise added to the mixture with stirring. The resulting mixture was stirred for 1 hour at the room temperature and a solid was precipitated. The solid was separated by filtration and dried at reduced pressure to give Compound 4 (91% yield). The crude solid product was directly used in the next reaction without purification.

Example 4

Preparation of Compound 4 (N-[3-chloro-4-(pyridin-2-ylmethoxy)]phenyl-2-cyanoacetamide)

55 mmol of Compound 2, 50 mmol of Compound 3a, 70 mmol of methanesulfonic acid and 120 mL of isopropanol were added into a reaction flask. The reaction system was heated to 80° C. with stirring, and was continuously stirred at this temperature for reaction. The reaction process was monitored by TLC. After reaction was completed, the reaction solution was cooled to room temperature, 120 mL of ice water was added to the reaction solution before 10 mL of ammonia water was dropwise added to the mixture with stirring. The resulting mixture was stirred for 1 hour at the room temperature and a solid was precipitated. The solid was separated by filtration and dried at reduced pressure to give Compound 4 (83% yield). The crude solid product was directly used in the next reaction without purification.

Example 5

Preparation of Compound 4 (N-[3-chloro-4-(pyridin-2-ylmethoxy)]phenyl-2-cyanoacetamide)

55 mmol of Compound 2, 50 mmol of Compound 3c, 70 mmol of methanesulfonic acid and 120 mL of isopropanol were added into a reaction flask. The reaction system was heated to 80° C. with stirring, and was continuously stirred at this temperature for reaction. The reaction process was monitored by TLC. After reaction was completed, the reaction solution was cooled to room temperature, 120 mL of ice water was added to the reaction solution before 10 mL of ammonia water was dropwise added to the mixture with stirring. The resulting mixture was stirred for 1 hour at the room temperature and a solid was precipitated. The solid was separated by filtration and dried at reduced pressure to give Compound 4 (86% yield). The crude solid product was directly used in the next reaction without purification.

Example 6

Preparation of Compound 4 (N-[3-chloro-4-(pyridin-2-ylmethoxy)]phenyl-2-cyanoacetamide)

58 mmol of Compound 2, 50 mmol of Compound 3a, 50 mmol of p-toluenesulfonic acid and 120 mL of isopropanol were added into a reaction flask. The reaction system was heated to 80° C. with stirring, and was continuously stirred at this temperature for reaction. The reaction process was monitored by TLC. After reaction was completed, the reaction solution was cooled to room temperature, 120 mL of ice water was added to the reaction solution before 10 mL of ammonia water was dropwise added to the mixture with stirring. The resulting mixture was stirred for 1 hour at the room temperature and a solid was precipitated. The solid was separated by filtration and dried at reduced pressure to give Compound 4 (71% yield). The crude solid product was directly used in the next reaction without purification.

Example 7

Preparation of Compound 4 (N-[3-chloro-4-(pyridin-2-ylmethoxy)]phenyl-2-cyanoacetamide)

58 mmol of Compound 2, 50 mmol of Compound 3c, 50 mmol of p-toluenesulfonic acid and 120 mL of isopropanol were added into a reaction flask. The reaction system was heated to 80° C. with stirring, and was continuously stirred at this temperature for reaction. The reaction process was monitored by TLC. After reaction was completed, the reaction solution was cooled to room temperature, 120 mL of ice water was added to the reaction solution before 10 mL of ammonia water was dropwise added to the mixture with stirring. The resulting mixture was stirred for 1 hour at the room temperature and a solid was precipitated. The solid was separated by filtration and dried at reduced pressure to give Compound 4 (78% yield). The crude solid product was directly used in the next reaction without purification.

Example 8

Preparation of Compound 4 (N-[3-chloro-4-(pyridin-2-ylmethoxy)]phenyl-2-cyanoacetamide)

58 mmol of Compound 2, 50 mmol of Compound 3a, 70 mmol of p-toluenesulfonic acid and 120 mL of isopropanol were added into a reaction flask. The reaction system was heated to 50° C. with stirring, and was continuously stirred at this temperature for reaction. The reaction process was monitored by TLC. After reaction was completed, the reaction solution was cooled to room temperature, 120 mL of ice water was added to the reaction solution before 10 mL of ammonia water was dropwise added to the mixture with stirring. The resulting mixture was stirred for 1 hour at the room temperature and a solid was precipitated. The solid was separated by filtration and dried at reduced pressure to give Compound 4 (63% yield). The crude solid product was directly used in the next reaction without purification.

Example 9

Preparation of Compound 4 (N-[3-chloro-4-(pyridin-2-ylmethoxy)]phenyl-2-cyanoacetamide)

58 mmol of Compound 2, 50 mmol of Compound 3c, 70 mmol of p-toluenesulfonic acid and 120 mL of isopropanol were added into a reaction flask. The reaction system was heated to 50° C. with stirring, and was continuously stirred at this temperature for reaction. The reaction process was monitored by TLC. After reaction was completed, the reaction solution was cooled to room temperature, 120 mL of ice water was added to the reaction solution before 10 mL of ammonia water was dropwise added to the mixture with stirring. The resulting mixture was stirred for 1 hour at the room temperature and a solid was precipitated. The solid was separated by filtration and dried at reduced pressure to give Compound 4 (70% yield). The crude solid product was directly used in the next reaction without purification.

Example 10

Preparation of Compound 5 (6-nitro-4-[[3-chloro-4-(pyridin-2-ylmethoxy) phenyl]amino]-7-ethoxylquinoline 3-carbonitrile)

In nitrogen atmosphere, 100 mmol of Compound 4 obtained in Example 1, 130 mmol of triethyl orthoformate, 120 mmol of 4-nitro-3-ethoxylphenylamine and 200 mL of absolute ethanol were added in a reaction flask. The reaction system was heated at reflux with stirring, and stirred at this temperature for reaction. The reaction process was monitored by TLC. After reaction was completed, the reaction solution was cooled to room temperature, and the precipitated solid was separated by filtration. The crude solid product was dissolved in 200 mL of diethylene glycol dimethyl ether with stirring before 300 mmol of aluminium chloride was added. The reaction system was heated to 140° C. and stirred for reaction. The reaction process was monitored by TLC. After reaction was completed, the reaction mixture was cooled to room temperature, and poured into 300 mL of ice water. The resulting mixture was stirred for 0.5 h and a solid was precipitated. The solid was separated by filtration and dried at reduced pressure to give Compound 5 (87% yield). The crude solid product was directly used in the next reaction without purification. A small amount of the crude solid product was purified for structure confirmation. ESI-LRMS m/z: 476.7 [M+H]$^+$, $^1$H NMR (500 MHz, DMSO-d6) δ1.34 (t, J=5.6 Hz, 2.8Hz, 3H), 3.99 (q, 2H), 5.55 (s, 2H), 6.25 (d, J=2.6 Hz, 1H), 6.34 (s, 1H), 6.49(d, J=2.6 Hz, 1H), 7.35-7.49(m, 2H), 7.75 (d, J=3.6 Hz, 1H), 8.07(t, J=3.6 Hz, 2.8Hz, 1H), 8.57(s, 1H), 8.66 (d, J=2.8 Hz, 1H), 9.56(s, 1H), 9.98 (s, 1H).

Example 11

Preparation of Compound 5 (6-nitro-4-[[3-chloro-4-(pyridin-2-ylmethoxy)phenyl]amino]-7-ethoxylquinoline 3-carbonitrile)

In nitrogen atmosphere, 50 mmol of Compound 4 obtained in Example 1, 52.5 mmol of triethyl orthoformate, 52.5 mmol of 4-nitro-3-ethoxylphenylamine and 100 mL of absolute ethanol were added in a reaction flask. The reaction system was heated at reflux with stirring, and stirred at this temperature for reaction. The reaction process was monitored by TLC. After reaction was completed, the reaction solution was cooled to room temperature, and the precipitated solid was separated by filtration. The crude solid product was dissolved in 100 mL of diethylene glycol dimethyl ether with stirring before 150 mmol of aluminium chloride was added. The reaction system was heated to 140° C. and stirred for reaction. The reaction process was monitored by TLC. After reaction was completed, the reaction mixture was cooled to room temperature, and poured into 150 mL of ice water. The resulting mixture was stirred for 0.5 h and a solid was precipitated. The solid was separated by filtration and dried at reduced pressure to give Compound 5 (79% yield). The crude solid product was directly used in the next reaction without purification.

Example 12

Preparation of Compound 5 (6-nitro-4-[[3-chloro-4-(pyridin-2-ylmethoxy)phenyl]amino]-7-ethoxylquinoline 3-carbonitrile)

In nitrogen atmosphere, 50 mmol of Compound 4 obtained in Example 1, 65 mmol of triethyl orthoformate, 60 mmol of 4-nitro-3-ethoxylphenylamine and 100 mL of absolute ethanol were added in a reaction flask. The reaction system was heated at reflux with stirring, and stirred at this temperature for reaction. The reaction process was monitored by TLC. After reaction was completed, the reaction solution was cooled to room temperature, and the precipitated solid was separated by filtration. The crude solid product was dissolved in 100 mL of diethylene glycol dimethyl ether with stirring before 150 mmol of ferric chloride was added. The reaction system was heated to 140° C. and stirred for reaction. The reaction process was monitored by TLC. After reaction was completed, the reaction mixture was cooled to room temperature, and poured into 150 mL of ice water. The resulting mixture was stirred for 0.5 h and a solid was precipitated. The solid was separated by filtration and dried at reduced pressure to give Compound 5 (65% yield). The crude solid product was directly used in the next reaction without purification.

Example 13

Preparation of Compound 5 (6-nitro-4-[[3-chloro-4-(pyridin-2-ylmethoxy)phenyl]amino]-7-ethoxylquinoline 3-carbonitrile)

In nitrogen atmosphere, 50 mmol of Compound 4 obtained in Example 1, 65 mmol of triethyl orthoformate, 60 mmol of 4-nitro-3-ethoxylphenylamine and 100 mL of absolute ethanol were added in a reaction flask. The reaction system was heated at reflux with stirring, and stirred at this temperature for reaction. The reaction process was monitored by TLC. After reaction was completed, the reaction solution was cooled to room temperature, and the precipitated solid was separated by filtration. The crude solid product was dissolved in 100 mL of diethylene glycol dimethyl ether with stirring before 150 mmol of zinc chloride was added. The reaction system was heated to 140° C. and stirred for reaction. The reaction process was monitored by TLC. After reaction was completed, the reaction mixture was cooled to room temperature, and poured into 150 mL of ice water. The resulting mixture was stirred for 0.5 h and a solid was precipitated. The solid was separated by filtration and dried at reduced pressure to give Compound 5 (78% yield). The crude solid product was directly used in the next reaction without purification.

Example 14

Preparation of Compound 5 (6-nitro-4-[[3-chloro-4-(pyridin-2-ylmethoxy) phenyl]amino]-7-ethoxylquinoline 3-carbonitrile)

In nitrogen atmosphere, 50 mmol of Compound 4 obtained in Example 1, 65 mmol of triethyl orthoformate, 60 mmol of 4-nitro-3-ethoxylphenylamine and 100 mL of absolute ethanol were added in a reaction flask. The reaction system was heated at reflux with stirring, and stirred at this temperature for reaction. The reaction process was monitored by TLC. After reaction was completed, the reaction solution was cooled to room temperature, and the precipitated solid was separated by filtration. The crude solid product was dissolved in 100 mL of diethylene glycol dimethyl ether with stirring before 150 mmol of boron trifluoride was added. The reaction system was heated to 140° C. and stirred for reaction. The reaction process was monitored by TLC. After reaction was completed, the reaction mixture was cooled to room temperature, and poured into 150 mL of ice water. The resulting mixture was stirred for 0.5 h and a solid was precipitated. The solid was separated by filtration and dried at reduced pressure to give Compound 5 (86% yield). The crude solid product was directly used in the next reaction without purification.

Example 15

Preparation of Compound 5 (6-nitro-4-[[3-chloro-4-(pyridin-2-ylmethoxy) phenyl]amino]-7-ethoxylquinoline 3-carbonitrile)

In nitrogen atmosphere, 50 mmol of Compound 4 obtained in Example 1, 65 mmol of triethyl orthoformate, 60 mmol of 4-nitro-3-ethoxylphenylamine and 100 mL of absolute ethanol were added in a reaction flask. The reaction system was heated at reflux with stirring, and stirred at this temperature for reaction. The reaction process was monitored by TLC. After reaction was completed, the reaction solution was cooled to room temperature, and the precipitated solid was separated by filtration. The crude solid product was dissolved in 100 mL of diethylene glycol dimethyl ether with stirring before 150 mmol of aluminium chloride was added. The reaction system was heated to 90° C. and stirred for reaction. The reaction process was monitored by TLC. After reaction was completed, the reaction mixture was cooled to room temperature, and poured into 150 mL of ice water. The resulting mixture was stirred for 0.5 h and a solid was precipitated. The solid was separated by filtration and dried at reduced pressure to give Compound 5 (57% yield). The crude solid product was directly used in the next reaction without purification.

Example 16

Preparation of Compound 5 (6-nitro-4-[[3-chloro-4-(pyridin-2-ylmethoxy)phenyl]amino]-7-ethoxylquinoline 3-carbonitrile)

In nitrogen atmosphere, 50 mmol of Compound 4 obtained in Example 1, 65 mmol of triethyl orthoformate, 60 mmol of 4-nitro-3-ethoxylphenylamine and 100 mL of absolute ethanol were added in a reaction flask. The reaction system was heated at reflux with stirring, and stirred at this temperature for reaction. The reaction process was monitored by TLC. After reaction was completed, the reaction solution was cooled to room temperature, and the precipitated solid was separated by filtration. The crude solid product was dissolved in 100 mL of diethylene glycol dimethyl ether with stirring before 100 mmol of aluminium chloride was added. The reaction system was heated to 140° C. and stirred for reaction. The reaction process was monitored by TLC.

After reaction was completed, the reaction mixture was cooled to room temperature, and poured into 150 mL of ice water. The resulting mixture was stirred for 0.5 h and a solid was precipitated. The solid was separated by filtration and dried at reduced pressure to give Compound 5 (64% yield). The crude solid product was directly used in the next reaction without purification.

Example 17

Preparation of Compound 1 (6-amino-4-[[3-chloro-4-(pyridin-2-ylmethoxy)phenyl]amino]-7-ethoxylquinoline 3-carbonitrile)

20 mmol of Compound 5 obtained in Example 10, 40 mL of ethanol and 40 mL of distilled water were added in a reaction flask. The mixture was heated to 50-60° C. before 1.0 g of activated carbon, 3.3 mmol of ferric chloride hexahydrate and 1.3 mmol of aluminium chloride hexahydrate were added. The mixture was heated to 75-80° C. after stirring, and 40 mmol of 80% hydrazine hydrate was slowly and dropwise added. The reaction system was incubated at this temperature for reaction. The reaction process was monitored by TLC. After reaction was completed, the reaction mixture was cooled to room temperature and filtered. The residue was washed with ethanol (5 mL×3), and the filtrate and the washings were combined and evaporated at reduced pressure to give a crude solid product. The crude solid product was slurried in 50 mL of distilled water. The mixture was filtered and the residue was dried at reduced pressure to give Compound 1 (86% yield). The structure of Compound 1 was confirmed by MS and HNMR. ESI-LRMS m/z: 446.6 [M+H]$^+$, 1H NMR (500 MHz, DMSO-d6) δ: 1.32 (t, J=5.6 Hz, 2.8Hz, 3H), 3.98 (q, 2H), 5.54 (s, 2H), 6.25 (d, J=2.6 Hz, 1H), 6.35 (s, 1H), 6.47(d, J=2.6 Hz, 1H), 6.73 (s, 1H),7.12 (s, 1H), 7.38-7.44(m, 1H), 7.76 (d, J=3.6 Hz, 1H), 8.07(t, J=3.6 Hz, 2.8Hz, 1H), 8.65 (d, J=2.8 Hz, 1H), 9.05(s, 1H), 9.58 (s, 2H), 9.87 (s, 1H).

Example 18. Preparation of Compound 1 (6-amino-4-[[3-chloro-4-(pyridin-2-ylmethoxy)phenyl]amino]-7-ethoxylquinoline 3-carbonitrile)

20 mmol of Compound 5 obtained in Example 10, 40 mL of ethanol and 40 mL of distilled water were added in a reaction flask. The mixture was heated to 50-60° C. before 0.8 g of activated carbon, 2 mmol of ferric chloride hexahydrate and 0.2 mmol of aluminium chloride hexahydrate were added. The mixture was heated to 75-80° C. after stirring, and 40 mmol of 80% hydrazine hydrate was slowly and dropwise added. The reaction system was incubated at this temperature for reaction. The reaction process was monitored by TLC. After reaction was completed, the reaction mixture was cooled to room temperature and filtered. The residue was washed with ethanol (5 mL×3), and the filtrate and the washings were combined and evaporated at reduced pressure to give a crude solid product. The crude solid product was slurried in 50 mL of distilled water. The mixture was filtered and the residue was dried at reduced pressure to give Compound 1 (81% yield).

Example 19

Preparation of Compound 1 (6-amino-4-[[3-chloro-4-(pyridin-2-ylmethoxy)phenyl]amino]-7-ethoxylquinoline 3-carbonitrile)

20 mmol of Compound 5 obtained in Example 10, 40 mL of ethanol and 40 mL of distilled water were added in a reaction flask. The mixture was heated to 50-60° C. before 1.0 g of activated carbon, 3.3 mmol of ferric chloride hexahydrate and 1.3 mmol of aluminium chloride hexahydrate were added. The mixture was heated to 50-55° C. after stirring, and 40 mmol of 80% hydrazine hydrate was slowly and dropwise added. The reaction system was incubated at this temperature for reaction. The reaction process was monitored by TLC. After reaction was completed, the reaction mixture was cooled to room temperature and filtered. The residue was washed with ethanol (5 mL×3), and the filtrate and the washings were combined and evaporated at reduced pressure to give a crude solid product. The crude solid product was slurried in 50 mL of distilled water. The mixture was filtered and the residue was dried at reduced pressure to give Compound 1 (69% yield).

Example 20

Preparation of Compound 1 (6-amino-4-[[3-chloro-4-(pyridin-2-ylmethoxy)phenyl]amino]-7-ethoxylquinoline 3-carbonitrile)

20 mmol of Compound 5 obtained in Example 10, 40 mL of ethanol and 40 mL of distilled water were added in a reaction flask. The mixture was heated to 50-60° C. before 1.0 g of activated carbon, 3.3 mmol of ferric chloride hexahydrate and 1.3 mmol of aluminium chloride hexahydrate were added. The mixture was heated to 85-90° C. after stirring, and 40 mmol of 80% hydrazine hydrate was slowly and dropwise added. The reaction system was incubated at this temperature for reaction. The reaction process was monitored by TLC. After reaction was completed, the reaction mixture was cooled to room temperature and filtered. The residue was washed with ethanol (5 mL×3), and the filtrate and the washings were combined and evaporated at reduced pressure to give a crude solid product. The crude solid product was slurried in 50 mL of distilled water. The mixture was filtered and the residue was dried at reduced pressure to give Compound 1 (90% yield).

What is claimed is:
1. A method of preparing 6-amino-4-[[3-chloro-4-(pyridin-2-ylmethoxy)phenyl]amino]-7-ethoxylquinoline 3-carbonitrile, comprising steps below:

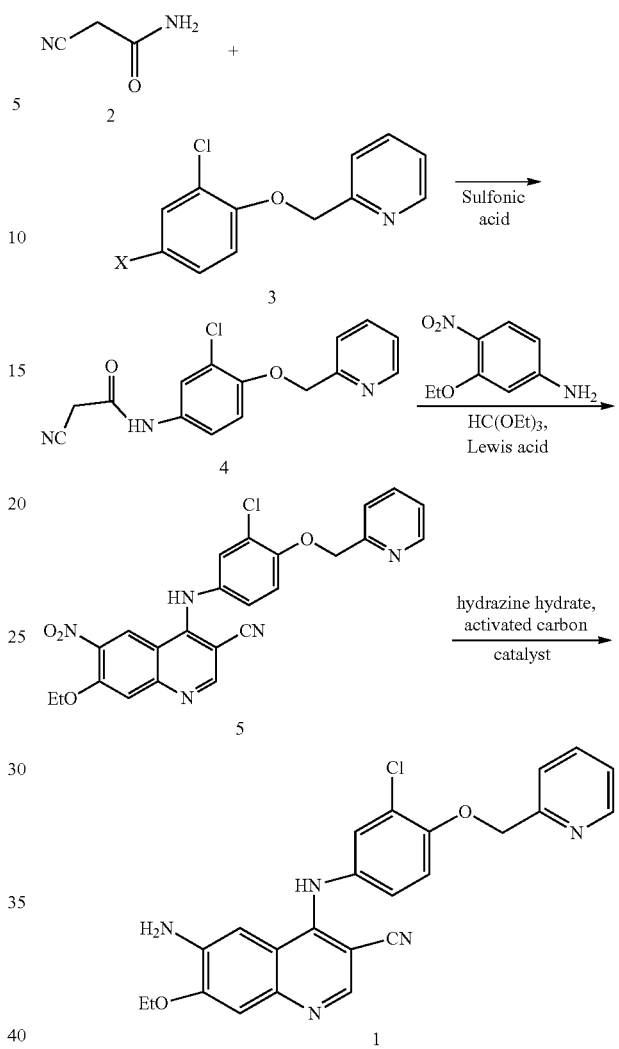

wherein, in step 1, reacting compound 3 and compound 2 in the presence of a sulfonic acid compound to give compound 4, wherein the compound 4 is N-[3-chloro-4-(pyridin-2-ylmethoxy)]phenyl-2-cyanoacetamide, and X in compound 3 is Br;
in step 2, reacting the compound 4, 4-nitro-3-ethoxylphenylamine and triethyl orthoformate by heating at reflux to give a solid intermediate; heating the solid intermediate and a Lewis acid for a ring-closing reaction to give compound 5; and
in step 3, reacting the compound 5, hydrazine hydrate and activated carbon in the presence of a catalyst to give compound 1,
wherein the catalyst in the step 3 is ferric chloride hexahydrate and aluminium chloride hexahydrate in a molar ratio of 1:(0.1-0.4).
2. The method according to claim 1, wherein a reaction temperature in the step 1 is 50-80° C., and the sulfonic compound is selected from an alkyl sulfonic acid and an aryl sulfonic acid.
3. The method according to claim 1, wherein a reaction in the step 1 is performed in isopropanol, and a molar ratio of the sulfonic compound to the compound 3 is (1.0-1.4):1; after the reaction in the step 1 is completed, the reaction is quenched, and ammonia water is added to precipitate a solid of the compound 4.

4. The method according to claim 1, wherein the Lewis acid in the step 2 is selected from aluminium chloride, ferric chloride, boron trifluoride and zinc chloride.

5. The method according to claim 1, wherein a temperature of the heating ring-closing reaction of the solid intermediate and the Lewis acid in the step 2 is 90-140° C.

6. The method according to claim 1, wherein a molar ratio of triethyl orthoformate to 4-nitro-3-ethoxylphenylamine to the Lewis acid to the compound 4 in the step 2 is (1.05-1.3):(1.05-1.2):(2-3):1.

7. The method according to claim 1, wherein the reaction of the compound 4, 4-nitro-3-ethoxylphenylamine and triethyl orthoformate in the step 2 is performed in ethanol; the solid intermediate and the Lewis acid react in diethylene glycol dimethyl ether; after the reaction in the step 2 is completed to obtain a reaction mixture, the reaction mixture is mixed with ice water to precipitate a solid of the compound 5.

8. The method according to claim 1, wherein a molar ratio of ferric chloride hexahydrate to the compound 5 in the step 3 is 1:(6-10); a reaction temperature in the step 3 is 50-90° C.

9. The method according to claim 1, wherein the reaction in the step 3 is performed in a mixed solvent of ethanol and water.

10. The method according to claim 9, wherein the step 3 comprises:
mixing the compound 5 with the mixed solvent of ethanol and water to obtain a mixture, heating the mixture to 50-90° C., adding activated carbon and the catalyst, and raising a temperature to 50-90° C.; and
continuously adding hydrazine hydrate, and reacting the mixture at 50-90° C. to give the compound 1.

11. The method according to claim 1, wherein a molar ratio of the sulfonic compound to the compound 3 in the step 1 is 1.4:1, and a reaction temperature in the step 1 is 80° C.;
a molar ratio of triethyl orthoformate to 4-nitro-3-ethoxylphenylamine to the Lewis acid to the compound 4 in the step 2 is 1.3:1.2:3:1, and the Lewis acid is selected from aluminium chloride and boron trifluoride; a temperature of the heating ring-closing reaction of the solid intermediate and the Lewis acid is 140° C.; and
the step 3 comprises: mixing the compound 5 with a mixed solvent of ethanol and water to obtain a mixture, and heating the mixture to 50-60° C.; adding activated carbon and the catalyst, and raising a temperature to 75-90° C.; continuously adding hydrazine hydrate, and reacting the mixture at 75-90° C. to give the compound 1.

* * * * *